(12) United States Patent
Haam et al.

(10) Patent No.: US 9,815,945 B2
(45) Date of Patent: Nov. 14, 2017

(54) BIOMARKER SPECIFIC AMPHIPHILIC NANOPARTICLES

(71) Applicant: University-Industry Foundation, Yonsei University, Seoul (KR)

(72) Inventors: SeungJoo Haam, Seoul (KR); Yong-min Huh, Seoul (KR); Jin-Suck Suh, Seoul (KR); Jaemoon Yang, Seoul (KR); Hyun-Ouk Kim, Seoul (KR); Jihye Choi, Incheon (KR); Eunji Jang, Seoul (KR); Byunghoon Kang, Seoul (KR); Ilkoo Noh, Seoul (KR); Seo Ryung Bae, Seoul (KR)

(73) Assignee: University-Industry Foundation, Yonsei University (KR)

( * ) Notice: Subject to any disclaimer, the term of this patent is extended or adjusted under 35 U.S.C. 154(b) by 0 days.

(21) Appl. No.: 14/421,646

(22) PCT Filed: Nov. 12, 2014

(86) PCT No.: PCT/KR2014/010871
§ 371 (c)(1),
(2) Date: Jul. 12, 2016

(87) PCT Pub. No.: WO2015/133703
PCT Pub. Date: Sep. 11, 2015

(65) Prior Publication Data
US 2017/0183454 A1    Jun. 29, 2017

(30) Foreign Application Priority Data

Mar. 6, 2014  (KR) .......................... 10-2014-0026541

(51) Int. Cl.
*C08G 81/00* (2006.01)
*A61K 9/16* (2006.01)
*A61K 9/127* (2006.01)
*A61K 9/107* (2006.01)

(52) U.S. Cl.
CPC ............ *C08G 81/00* (2013.01); *A61K 9/1075* (2013.01); *A61K 9/1273* (2013.01); *A61K 9/1641* (2013.01)

(58) Field of Classification Search
None
See application file for complete search history.

(56) References Cited

U.S. PATENT DOCUMENTS

2012/0135070 A1    5/2012  Kros et al.

FOREIGN PATENT DOCUMENTS

| JP | 2007-524663 | 8/2007 |
| KR | 10-2001-0035265 | 11/2007 |
| KR | 10-2010-0112964 | 4/2014 |

*Primary Examiner* — Brian J Davis
(74) *Attorney, Agent, or Firm* — Cooley LLP; Ivor Elrifi; Matthew Pavao

(57) ABSTRACT

The present invention relates to an amphiphilic nanoparticle specific to a biomarker, and more particularly, provides an amphiphilic nanoparticle which may be used as a diagnosis or treatment-type drug or gene carrier by selectively recognizing a proteolytic enzyme specifically expressed in a cellular membrane of a specific cell, and then being bound to the proteolytic enzyme to efficiently achieve the intracellular uptake and selective cleavage. The amphiphilic nanoparticle of the present invention may be used in the diagnosis or therapy of a disease.

17 Claims, 15 Drawing Sheets

SEQUENCE LISTING

```
<160> NUMBER OF SEQ ID NOS: 13

<210> SEQ ID NO 1
<211> LENGTH: 11
<212> TYPE: PRT
<213> ORGANISM: Artificial Sequence
<220> FEATURE:
<223> OTHER INFORMATION: MT1-MMP specific peptide seqence

<400> SEQUENCE: 1

Gly Pro Leu Pro Leu Arg Ser Trp Gly Leu Lys
1               5                   10

<210> SEQ ID NO 2
<211> LENGTH: 5
<212> TYPE: PRT
<213> ORGANISM: Artificial Sequence
<220> FEATURE:
<223> OTHER INFORMATION: MMP-2/9 specific peptide seqence

<400> SEQUENCE: 2

Pro Leu Gly Leu Arg
1               5

<210> SEQ ID NO 3
<211> LENGTH: 7
<212> TYPE: PRT
<213> ORGANISM: Artificial Sequence
<220> FEATURE:
<223> OTHER INFORMATION: MMP-7 specific peptide seqence

<400> SEQUENCE: 3

Val Pro Leu Ser Leu Thr Met
1               5

<210> SEQ ID NO 4
<211> LENGTH: 6
<212> TYPE: PRT
<213> ORGANISM: Artificial Sequence
<220> FEATURE:
<223> OTHER INFORMATION: MMP-13 specific peptide seqence

<400> SEQUENCE: 4

Pro Leu Gly Met Arg Gly
1               5

<210> SEQ ID NO 5
<211> LENGTH: 2
<212> TYPE: PRT
<213> ORGANISM: Artificial Sequence
<220> FEATURE:
<223> OTHER INFORMATION: Cathepsins B specific peptide seqence
```

```
<400> SEQUENCE: 5

Lys Lys
1

<210> SEQ ID NO 6
<211> LENGTH: 7
<212> TYPE: PRT
<213> ORGANISM: Artificial Sequence
<220> FEATURE:
<223> OTHER INFORMATION: Cathepsins D specific peptide seqence

<400> SEQUENCE: 6

Pro Ile Cys Phe Phe Arg Leu
1               5

<210> SEQ ID NO 7
<211> LENGTH: 5
<212> TYPE: PRT
<213> ORGANISM: Artificial Sequence
<220> FEATURE:
<223> OTHER INFORMATION: v

<400> SEQUENCE: 7

His Ser Ser Leu Gln
1               5

<210> SEQ ID NO 8
<211> LENGTH: 4
<212> TYPE: PRT
<213> ORGANISM: Artificial Sequence
<220> FEATURE:
<223> OTHER INFORMATION: Caspase-1 specific peptide seqence

<400> SEQUENCE: 8

Trp Glu His Asp
1

<210> SEQ ID NO 9
<211> LENGTH: 4
<212> TYPE: PRT
<213> ORGANISM: Artificial Sequence
<220> FEATURE:
<223> OTHER INFORMATION: Caspase-3 specific peptide seqence

<400> SEQUENCE: 9

Asp Glu Val Asp
1

<210> SEQ ID NO 10
<211> LENGTH: 4
<212> TYPE: PRT
<213> ORGANISM: Artificial Sequence
<220> FEATURE:
<223> OTHER INFORMATION: Thrombin specific peptide seqence: the P letter
      means pipecolinic acid

<400> SEQUENCE: 10

Phe Pro Arg Ser
1

<210> SEQ ID NO 11
<211> LENGTH: 6
<212> TYPE: PRT
<213> ORGANISM: Artificial Sequence
<220> FEATURE:
<223> OTHER INFORMATION: Fijian specific peptide seqence
```

```
<400> SEQUENCE: 11

Asn Gln Glu Gln Val Ser
1               5

<210> SEQ ID NO 12
<211> LENGTH: 4
<212> TYPE: PRT
<213> ORGANISM: Artificial Sequence
<220> FEATURE:
<223> OTHER INFORMATION: DPP-IV specific peptide seqence

<400> SEQUENCE: 12

Gly Pro Gly Pro
1

<210> SEQ ID NO 13
<211> LENGTH: 10
<212> TYPE: PRT
<213> ORGANISM: Artificial Sequence
<220> FEATURE:
<223> OTHER INFORMATION: HIV protease specific peptide seqence

<400> SEQUENCE: 13

Gly Val Ser Gln Asn Tyr Pro Ile Val Gly
1               5                   10
```

BIOMARKER SPECIFIC AMPHIPHILIC NANOPARTICLES

CROSS-REFERENCE TO RELATED APPLICATIONS

This application is a national stage application, filed under 35 U.S.C. §371, of International Application No. PCT/KR2014/010871, filed on Nov. 12, 2014, which claims priority to, and the benefit of, Korean Patent Application No. 10-2014-0026541, filed Mar. 6, 2014. The contents of each application are incorporated by reference in their entirety.

TECHNICAL FIELD

The present invention relates to amphiphilic nanoparticles as a poly amino acid-based nanoplatform having a targeting ability specific to a biomarker.

BACKGROUND ART

In order to constitute a target directed-type nano delivery system in the related art, the following processes need to be performed: a process of forming a drug or gene nanovehicle which supports a drug or gene through the synthesis of an amphiphilic polymer, a process of binding a spacer which may improve binding stability of the formed nanovehicle to a targeting molecule, and finally, a process of binding a polymer nanovehicle to a spacer, and then binding the targeting molecule (see FIG. 1).

However, this technology is disadvantageous in that the processes are complicated and the unit cost for the products is high.

DISCLOSURE

Technical Problem

The present invention has been contrived to solve the aforementioned problems of the related art, and an object of the present invention is to provide an amphiphilic nanoparticle as a poly amino acid-based nanoplatform having a targeting ability specific to a biomarker without constituting a spacer through a single process.

Another object of the present invention has also been made in an effort to provide a pharmaceutical use of the amphiphilic nanoparticle.

Technical Solution

In order to accomplish the object, the present invention provides an amphiphilic nanoparticle including: a block copolymer containing a hydrophilic polymer and a hydrophobic polymer (A); and a block copolymer containing a peptide cleaved by a proteolytic enzyme and a hydrophobic polymer (B).

The present invention also provides a method for preparing an amphiphilic nanoparticle of the present invention, the method including: reacting a block copolymer containing a hydrophilic polymer and a hydrophobic polymer (A) with a block copolymer containing a peptide cleaved by a proteolytic enzyme and a hydrophobic polymer (B).

The present invention also provides a composition for activity or quantitative analysis of a proteolytic enzyme, including the amphiphilic nanoparticle of the present invention.

The present invention also provides a target directed-type contrast agent composition including: the amphiphilic nanoparticle of the present invention; and a pharmaceutically acceptable carrier.

The present invention also provides a contrast agent composition for simultaneous diagnosis or treatment, including: the amphiphilic nanoparticle of the present invention; and a pharmaceutically acceptable carrier.

The present invention also provides a multi-diagnosis probe including: the amphiphilic nanoparticle of the present invention; and a diagnosis probe for image interpretation.

Advantageous Effects

According to the present invention, it is possible to use a poly amino acid-based amphiphilic nanoparticle having a targeting ability specific to a biomarker as a diagnostic or therapeutic drug or gene carrier by selectively recognizing a proteolytic enzyme specifically expressed in a specific cellular membrane, and then binding the amphiphilic nanoparticle to the proteolytic enzyme to efficiently achieve the intracellular uptake and selective cleavage.

Further, the amphiphilic nanoparticle of the present invention has a peptide specific to a biomarker, and thus may achieve selective diagnosis or treatment.

BEST MODE

Hereinafter, the configuration of the present invention will be described in detail.

The present invention relates to an amphiphilic nanoparticle including: a block copolymer containing a hydrophilic polymer and a hydrophobic polymer (A); and a block copolymer containing a peptide cleaved by a proteolytic enzyme and a hydrophobic polymer (B).

Further, the present invention provides a method for preparing the amphiphilic nanoparticle, the method including: reacting a block copolymer containing a hydrophilic polymer and a hydrophobic polymer (A) with a block copolymer containing a peptide cleaved by a proteolytic enzyme and a hydrophobic polymer (B).

The amphiphilic nanoparticle of the present invention may be used as a diagnostic or therapeutic drug or gene carrier by forming a self-assembly or self-aggregate through the balance of hydrophobic and hydrophilic molecules, by selectively being recognized a proteolytic enzyme specifically expressed in a cellular membrane of a specific cell by a biomarker specific peptide, that is, a peptide cleaved by the proteolytic enzyme, and being bound to the proteolytic enzyme to introduce the amphiphilic nanoparticle into cells, and then being selectively cleaved by the proteolytic enzyme to transfer a support material, for example, a diagnosis reagent, drug, or gene, and the like to cells.

Figure 1:
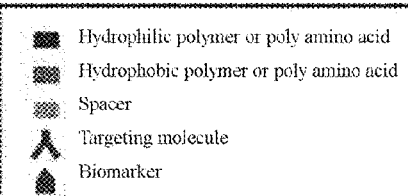
FIG. 1 illustrates the action mechanisms of a nanovehicle for diagnosis or treatment of cancer in the related art and an amphiphilic nanoparticle of the present invention.
Figure 1:
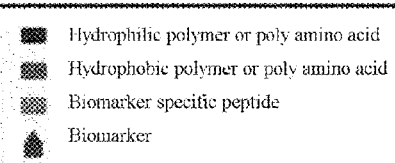
Figure 1:
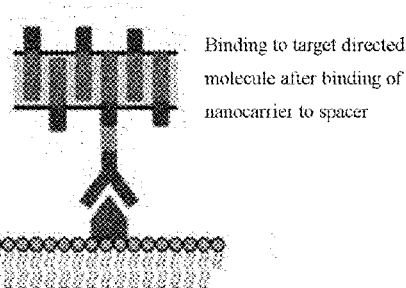
Figure 1:
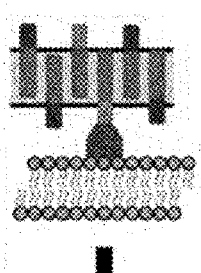
Figure 1:
Figure 2:
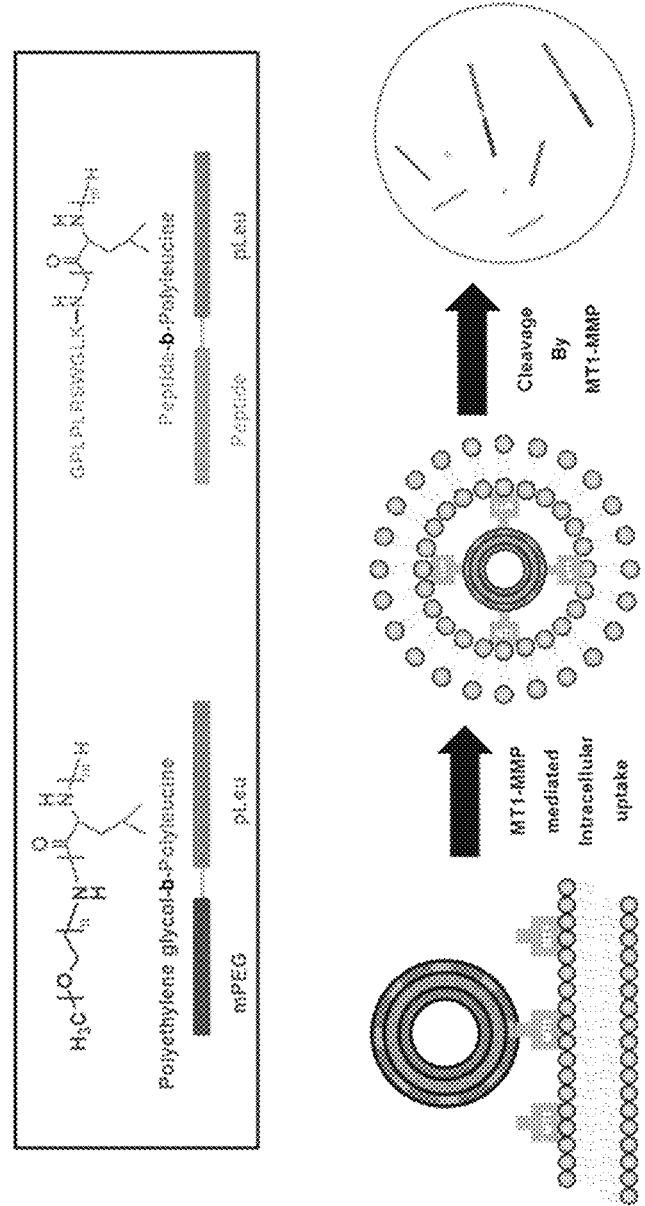
FIG. 2 illustrates an amphiphilic block copolymer for preparing the amphiphilic nanoparticle of the present invention (top) and the intracellular uptake and selective cleavage of the amphiphilic nanoparticle in a tumor microenvironment (bottom).

FIG. 1 illustrates the action mechanisms of a nanovehicle for diagnosis or treatment of cancer in the related art and an amphiphilic nanoparticle of the present invention, FIG. 2 illustrates an amphiphilic block copolymer for preparing the amphiphilic nanoparticle of the present invention (top) and the intracellular uptake and selective cleavage of the amphiphilic nanoparticle (pepti-polymersome) in a tumor microenvironment (bottom), and the pepti-polymersome is a nanovehicle by selectively recognizing a biomarker MT1-MMP specifically expressed in a cellular membrane of cancer, and then being bound to the biomarker to efficiently achieve intracellular uptake and selective cleavage.

The term "pepti-polymersome" used in the present specification refers to a polymersome selectively having a targeting ability specific to a biomarker expressed in a specific cell or tissue while forming the polymersome because a biomarker specific peptide is bound to a block copolymer. In particular, when the amphiphilic nanoparticle of the present invention forms a polymersome structure, the structure is referred to as a pepti-polymersome.

Further, the term "pepti-micelle" is used when the amphiphilic nanoparticle of the present invention forms a micelle structure.

The amphiphilic nanoparticle of the present invention includes a peptide specifically cleaved by a proteolytic enzyme in a block copolymer, and thus has a targeting ability to the proteolytic enzyme without a spacer configuration. Accordingly, the amphiphilic nanoparticle of the present invention has an advantage in that production unit price may be reduced through a single process. Further, in relation to cancer, osteoarthritis, rheumatoid arthritis, dementia, or atherosclerosis, the amphiphilic nanoparticle of the present invention has a targeting ability to a proteolytic enzyme specifically expressed in a cellular membrane in cells around a lesion site, and thus may be usefully used for diagnosis or treatment of the above-mentioned diseases.

The block copolymer (A) may be an amphiphilic block copolymer prepared through a chemical bond of a hydrophilic polymer and a hydrophobic polymer.

As the hydrophilic polymer, it is possible to use one or two or more of polyalkylene glycol, polyethylene oxide, polyoxazoline, poly(N-vinylpyrrolidone), polyvinyl alcohol, polyhydroxyethylmethacrylate, dextran, polyserine, polythreonine, polytyrosine, polylysine, polyarginine, polyhistidine, polyaspartic acid, or polyglutamic acid. Preferably, it is possible to use a polyalkylene glycol having a molecular weight of 1,000 to 5,000, or derivatives thereof, and the like. More preferably, it is possible to use a methoxy amino polyethylene glycol having a molecular weight of 1,000 to 5,000. The hydrophilic polymer may be appropriately modified for bonding to a hydrophobic polymer by using a publicly known technology. According to an exemplary embodiment, the hydrophilic polymer may be used in a form of mPEG-NH$_2$ via a modification process of mPEG-OH→mPEG-TsCl→mPEG-N$_3$→mPEG-NH$_2$.

The hydrophilic nanoparticle may have a mass fraction of 25 to 40 calculated by the following Equation 1 so as for the amphiphilic nanoparticle of the present invention to form a polymersome.

brane-type 1 matrix metalloproteinase (MT1-MMP), and the like, thrombin, factor Xiiia (FXIIIa), caspase, urokinase plasminogen activator (uPA), Fijian, cathepsins, HIV protease, dipeptidyl peptidase (DPP-IV) or proteasome, and the like. Specifically, the peptide may be represented by any one of the amino acid sequences described in SEQ ID NOS: 1 to 13. More specifically, the peptide may be represented by the amino acid sequence described in SEQ ID NO: 1, which is specifically cleaved by membrane-type 1 matrix metalloproteinase.

Diseases associated with target proteolytic enzymes of the peptides cleaved by the proteolytic enzyme are as shown in the following Table 1.

TABLE 1

| Disease | Target proteolytic enzyme | Peptide matrix/ Cleavage site | SEQ ID NO. |
|---|---|---|---|
| Cancer | MT1-MMP | GPLPLRSW/GLK | 1 |
| | MMP-2/9 | PLG/LR | 2 |
| Arteriosclerosis | MMP-7 | VPLS/LTM | 3 |
| Rheumatoid arthritis | MMP-13 | PLG/MRG | 4 |
| | Cathepsin B | K/K | 5 |
| | Cathepsin D | PICF/FRL | 6 |
| | PSA | HSSLQ/ | 7 |
| Apoptosis | Caspase-1 | WEHD/ | 8 |
| | Caspase-3 | DEVD/ | 9 |
| Cardiovascular disease | Thrombin | F(Pip)R/S | 10 |
| | Fijian | NQ/EQVS | 11 |
| Diabetes | DPP-IV | GP/GP | 12 |
| HSV | HIV protease | GVSQNY/PIVG | 13 |

Mass fraction=Molecular weight of hydrophilic polymer or peptide/(Molecular weight of hydrophilic polymer or peptide+Molecular weight of hydrophobic polymer)  [Equation 1]

The hydrophilic nanoparticle may have a mass fraction of more than 40 and 70 or less calculated by Equation 1 so as for the amphiphilic nanoparticle of the present invention to form a micelle.

The hydrophobic polymer may be a homopoly amino acid represented by the following Chemical Formula 1:

(poly-M)$n$  [Chemical Formula 1]

Here,

M is leucine, isoleucine, valine, phenylalanine, proline, glycine, or methionine, and n represents 10 to 100.

According to an exemplary embodiment of the present invention, it is possible to synthesize mPEG-b-polyleucine (mPEG-b-pLeu) which is an amphiphilic block copolymer (A) through a peptide bond of the modified hydrophilic polymer and a hydrophobic polyleucine.

In addition, the block copolymer (B) may be synthesized as an amphiphilic block copolymer through a peptide bond of a peptide cleaved by a proteolytic enzyme and a hydrophobic polymer.

As the hydrophobic polymer, the above-described homopoly amino acid may be used.

The peptide cleaved by the proteolytic enzyme may be those specifically cleaved by a matrix metalloproteinases (MMPs) including MMP-2/9, MMP-7, MMP-13, mem- The peptide cleaved by the proteolytic enzyme may be appropriately synthesized, and for the synthesis, various peptide synthesis methods publicly known to a person with ordinary skill in the art, for example, an Fmoc strategy according to a solid phase synthesis may be used.

According to an exemplary embodiment of the present invention, MT1-MMP-b-pLeu, which is an amphiphilic block copolymer (B) may be synthesized by reacting a hydrophobic polymer polyleucine with Fmoc-MT1-MMP-NH$_2$, and then subjecting the reaction product to a deprotection for removal of Fmoc.

The peptide may have a mass fraction of 25 to 40 calculated by Equation 1 so as for the amphiphilic nanoparticle of the present invention to form a polymersome. Further, the peptide may have a mass fraction of more than 40 and 70 or less calculated by Equation 1 so as for the amphiphilic nanoparticle of the present invention to form a micelle.

The amphiphilic nanoparticle may be prepared by mixing the amphiphilic block copolymer (A) and the amphiphilic block copolymer (B) at an appropriate weight ratio, for example, (A):(B) of 10:90 to 50:50, and dispersing or dissolving the mixture in a solvent. For example, the amphiphilic nanoparticle may be prepared by using a method of dispersing the block copolymer (A) and the block copolymer (B) in an aqueous solution, and then applying ultrasonic waves, a method of dispersing or dissolving the block copolymers in an organic solvent, and then extracting the organic solvent with an excessive amount of water or evaporating the organic solvent, a method of dispersing or dissolving the block copolymers in an organic solvent, and then dialyzing the organic solvent with an excessive amount of water, a method of dispersing or dissolving the block copolymers in an organic solvent, and then vigorously evaporating the solvent using a homogenizer or a high pressure emulsifier, or a thin film hydration method, and the like.

As the organic solvent, it is possible to use chloroform, hexane, heptane, methylene chloride, benzene, toluene, tetrahydrofuran, acetone, or a mixture thereof, but the organic solvent is not particularly limited thereto.

According to an exemplary embodiment of the present invention, the amphiphilic nanoparticle may be prepared through the thin film hydration. That is, the amphiphilic nanoparticle may be formed by dissolving a block copolymer (A) and a block copolymer (B) in an organic solvent at a predetermined ratio, and then evaporating the organic solvent through a rotary vacuum evaporator, hydrating a thin film formed for a predetermined time, and then stirring the mixture.

The amphiphilic nanoparticles prepared via the process may have an average particle diameter of 200 nm or less. Preferably, the average particle diameter may be 50 to 200 nm.

The amphiphilic nanoparticle of the present invention may have a micelle structure in a form of spherical particles having a hydrophobic core and a hydrophilic shell through amphiphilic characteristics of block copolymers, or a polymersome structure in which a hydrophobic shell and a hydrophilic shell doubly surround a hollow hydrophilic core.

These structural forms may be prepared by controlling the mass fraction of the hydrophilic polymer (and peptide). For example, when the mass fraction of the hydrophilic polymer (and peptide) is 25 to 40, a polymersome is formed, and when the mass fraction is more than 40 and 70 or less, a micelle may be prepared.

In the micelle structure, a hydrophobic dye may be supported in a hollow hydrophobic core, and in the polymersome structure, a hydrophilic dye may be supported in a hollow hydrophilic core, and simultaneously, a hydrophobic dye may be supported in a hydrophobic shell. Accordingly, it can be known that the amphiphilic nanoparticle of the present invention is advantageous in that the amphiphilic nanoparticle of the present invention may be used as a drug carrier which may support hydrophilic and/or hydrophobic drugs.

Accordingly, the amphiphilic nanoparticle of the present invention may additionally include a fluorescent material for diagnosis.

The fluorescent material may be physically and chemically sealed or bound to a hydrophilic region or a hydrophobic region.

The fluorescent material may be a fluorescent substance which emits fluorescence in a visible light region or near-infrared region, and as an example, it is possible to use fluorescein, BODYPY, tetramethylrhodamine, Alexa, cyanine, allopicocyanine, or other fluorescent materials which generate fluorescence. Further, a fluorescent material having a high quantum yield may be used. In addition, the fluorescent material may be a hydrophilic or hydrophobic dye.

In addition, the amphiphilic nanoparticle of the present invention may further include a pharmaceutically active component for treating a disease.

The pharmaceutically active component may be physically and chemically sealed or bound to a hydrophilic region or a hydrophobic region.

The pharmaceutically active component is not particularly limited, but it is possible to use one or two or more of an anticancer drug, an antibiotic, a hormone, a hormone antagonist, interleukin, interferon, a growth factor, a tumor necrosis factor, endotoxin, lymphotoxin, urokinase, streptokinase, a tissue plasminogen activator, a protease inhibitor, alkyl phosphocholine, a component labeled with a radioactive isotope, a cardiovascular pharmaceutical, a gastrointestinal pharmaceutical, or a neuro pharmaceutical.

The present invention also relates to a composition for activity or quantitative analysis of a proteolytic enzyme including the amphiphilic nanoparticle of the present invention.

Since in the amphiphilic nanoparticle of the present invention, a peptide cleaved by a proteolytic enzyme may be easily modified and controlled, and thus a desired specific proteolytic enzyme and a desired wavelength range may be easily controlled, the amphiphilic nanoparticle of the present invention may be designed for various proteolytic enzymes, thereby achieving the activity or quantitative analysis of the above-described types of proteolytic enzymes.

The present invention also relates to a target directed-type contrast agent composition including: the amphiphilic nanoparticle of the present invention; and a pharmaceutically acceptable carrier.

Since the amphiphilic nanoparticle of the present invention is bound to a peptide specifically cleaved by a specific proteolytic enzyme, and thus may be directed to a target in a cell or tissue in which the proteolytic enzyme is present, the amphiphilic nanoparticle of the present invention may be used as a contrast agent which may achieve imaging of a target site through a magnetic resonance image device and optical image device, and the like.

The pharmaceutically acceptable carrier includes a carrier and a vehicle usually used in the medicine industry, and specifically includes an ion exchange resin, alumina, aluminum stearate, lecithin, a serum protein (for example, human serum albumin), buffer materials (for example, various phosphate, glycine, sorbic acid, potassium sorbate and partial glyceride mixtures of vegetable saturated fatty acids), water, a salt or an electrolyte (for example, protamine sulfate, disodium hydrogen phosphate, potassium hydrogen phosphate, sodium chloride, and a zinc salt), colloidal silica, magnesium trisilicate, polyvinyl pyrrolidone, a cellulose-based matrix, polyethylene glycol, sodium carboxylmethylcellulose, polyarylate, wax, polyethylene glycol or lanoline, but is not limited thereto.

Furthermore, the target directed-type contrast agent composition of the present invention may additionally include a lubricant, a wetting agent, an emulsifier, a suspending agent, or a preservative, in addition to the components.

As an aspect, the target directed-type contrast agent composition according to the present invention may be prepared in a form of aqueous solution for parenteral administration, and preferably, Hank's solution, Ringer's solution or a buffer solution such as physically buffered saline may be used. To the aqueous suspension for injection may be added a matrix which may increase the viscosity of suspension, such as sodium carboxymethylcellulose, sorbitol or dextran.

Another preferred aspect of the target directed-type contrast agent composition of the present invention may be in a form of sterile injectable formulation in an aqueous or oil suspension for sterile injection. Such a suspension may be formulated using a suitable dispersing agent or wetting agent (for example, Tween 80) and a suspending agent, according to the publicly known technique in the art.

In addition, the sterile injectable formulation may be a sterile injectable solution or suspension (for example, a solution in 1,3-butanediol) in a non-toxic, parenterally acceptable diluent or solvent. The vehicle and solvent which may be used include mannitol, water, Ringer's solution and an isotonic sodium chloride solution. Furthermore, sterile non-volatile oil is usually used as a solvent or a suspending medium. For this purpose, any less irritable non-volatile oil including synthetic mono or diglycerides may be used.

The target directed-type contrast agent composition of the present invention may be used to detect a signal generated from the amphiphilic nanoparticle when administered to tissues or cells separated from an object to be diagnosed and yield an image.

To detect the signal generated by the amphiphilic nanoparticle, a magnetic resonance image device (MRI) and an optical imaging device may be used.

The magnetic resonance image device is a device for emitting energy of an atomic nucleus such as hydrogen, converting the energy into a signal, and subjecting the signal to computer processing to convert the signal into an image by putting an organism in a powerful magnetic field, irradiating the organism with radio waves having a specific frequency, allowing an atomic nucleus such as hydrogen, which is present in a tissue of the organism to absorb energy to end up in the upper energy state, and then stopping the radio waves. Since the magnetic field or the radio waves do not interfere with bones, a clear three-dimensional tomographic imaging may be obtained longitudinally, transversely, and at an optional angle with regard to a tumor near hard bones, or a tumor of the brain or bone marrow. In particular, the magnetic resonance image device is preferably a T2 spin-spin relaxation magnetic resonance image device.

The present invention also relates to a contrast agent composition for simultaneous diagnosis or treatment, including: the amphiphilic nanoparticle of the present invention; and a pharmaceutically acceptable carrier.

The amphiphilic nanoparticle of the present invention may exhibit fluorescence in cells or tissues in which a proteolytic enzyme associated with a disease is expressed through physical and chemical sealing or bonding of a pharmaceutically active component and a fluorescent material, and thus may be used for a nano probe and a drug or gene delivery vehicle for separation of biological molecules, diagnosis or treatment, and the like through a magnetic resonance image device and an optical image device and the like.

Representative examples of in vivo diagnosis using the amphiphilic nanoparticle include molecular magnetic resonance image diagnosis or a magnetic relaxation sensor. The amphiphilic nanoparticle shows a better T2 contrasting effect as the size thereof is increased, and when these properties are used, the amphiphilic nanoparticle may be used as a sensor for detecting biological molecules. That is, specific biological molecules lead to aggregation of the amphiphilic nanoparticles, and accordingly, the T2 magnetic resonance image effect is increased. The biological molecule is detected using this difference.

Furthermore, the amphiphilic nanoparticle of the present invention may be used for diagnosis and/or treatment of various diseases associated with tumor, for example, squamous cell carcinoma, uterine cancer, uterine cervical cancer, prostatic cancer, head and neck cancer, pancreas cancer, brain tumor, breast cancer, liver cancer, skin cancer, esophageal cancer, testicular cancer, kidney cancer, large intestine cancer, rectal cancer, gastric cancer, kidney cancer, bladder cancer, ovarian cancer, cholangiocarcinoma and gallbladder cancer. Further, the amphiphilic nanoparticle of the present invention may be used for a method of imaging a proteolytic enzyme in an inflammatory disease such as rheumatoid arthritis and osteoarthritis, and an intractable disease including dementia, cerebral apoplexy, and the like.

The present invention also relates to a multi-diagnosis probe including: the amphiphilic nanoparticle of the present invention; and a diagnosis probe for image interpretation.

In the diagnosis probe, it is possible to use a T1 magnetic resonance image diagnosis probe, an optical diagnosis probe, a CT diagnosis probe, or a radioisotope, and the like.

For example, the multi-diagnosis probe may perform simultaneously T2 magnetic resonance image and T1 magnetic resonance image diagnosis when a T1 magnetic resonance image diagnosis probe is bound to a peptide cleaved by a proteolytic enzyme, may perform simultaneously magnetic resonance image and optical imaging when an optical diagnosis probe is bound to the peptide, and may perform simultaneously magnetic resonance image and CT diagnosis when a CT diagnosis probe is bound to the peptide. In addition, magnetic resonance image and PET and SPECT diagnosis may be simultaneously performed when a radioisotope is bound to the peptide.

The T1 magnetic resonance image diagnosis probe includes a Gd compound, or an Mn compound, the optical diagnosis probe includes an organic fluorescent dye, a quantum dot, or a dye labeled inorganic support (for example, $SiO_2$, $Al_2O_3$), the CT diagnosis probe includes an iodine (I) compound or gold nanoparticles, and the radioisotope includes In, Tc or F.

Hereinafter, the present invention is described in detail with reference to the Examples. However, the following Examples only illustrate the present invention, and the contents of the present invention are not limited by the following Examples.

BEST MODE

<Example 1> Preparation of Amphiphilic Nanoparticle (Preparation of Block Copolymer of Hydrophilic Polymer and Hydrophobic Polymer)

A block copolymer including a methoxy amino polyethylene glycol having a molecular weight of 2,000 (mPEG-$NH_2$, 0.2 mmol) as a hydrophilic polymer and polyleucine as a hydrophobic polymer was synthesized. In order to synthesize the polyleucine, the synthesis was performed by a Fuchs-Farthing method using leucine-N-carbonxyanhydride (Leu-NCA, 6.3 mmol) and triphosgene (11.43 mmol). In order to prepare Leu-NCA, DL-leucine was dissolved in THF at 40° C. under nitrogen, and then triphosgene was added thereto. After 3 hours, Leu-NCA obtained by precipitating the mixture in n-hexane was recrystallized from THF/n-hexane. After leucine-N-carbonxyanhydride was prepared, mPEG-b-polyleucine (mPEG-b-pLeu) was synthesized by adding Leu-NCA to a DMF solution of mPEG-$NH_2$ and maintaining the reaction at 35° C. under nitrogen for 24 hours. The synthesized block copolymer was separated through precipitation in diethyl ether.

(Preparation of Amphiphilic Block Copolymer of Peptide-Hydrophobic Polymer)

A peptide-b-polyleucine (MT1-MMP-b-pLeu) was synthesized by adding Z-L-Leucine N-carboxyanhydride (Leu-NCA, 15.2 mmol) to a solution of a MT1-MMP-NH$_2$ (SEQ ID NO:1, see FIG. 2) dissolved in DMF, which was selected as a biomarker-specific peptide and was a peptide cleaved by a proteolysis enzyme, and maintaining the reaction at 35° C. under nitrogen for 24 hours. The synthesized block copolymer was separated through precipitation in diethyl ether. A deprotection was performed to remove the Z group of the synthesized MT1-MMP-b-pLeu. For this purpose, trifluoroacetic acid (TFA) and HBr were added to the synthesized block copolymer. The product thus obtained was dialyzed for 24 hours and separated, and then freeze-dried.

(Formation of Pepti-Polymersome of Prepared Synthetic Product)

The amphiphilic block copolymers prepared above formed a pepti-polymersome through thin film hydration. First, synthesized amphiphilic block copolymers, mPEG-b-pLeu and MT1-MMP-b-pLeu, were dissolved in an organic solvent at a ratio of 50:50, and then the organic solvent was evaporated through a rotary vacuum evaporator in order to prepare a thin amphiphilic block copolymer film. A thin film formed was hydrated for 6 hours, and then stirred for 6 hours. The formed pepti-micelle and pepti-polymersome were confirmed through TEM and CLSM in FIGS. 10 and 11, and stored at 4° C.

Figure 3:
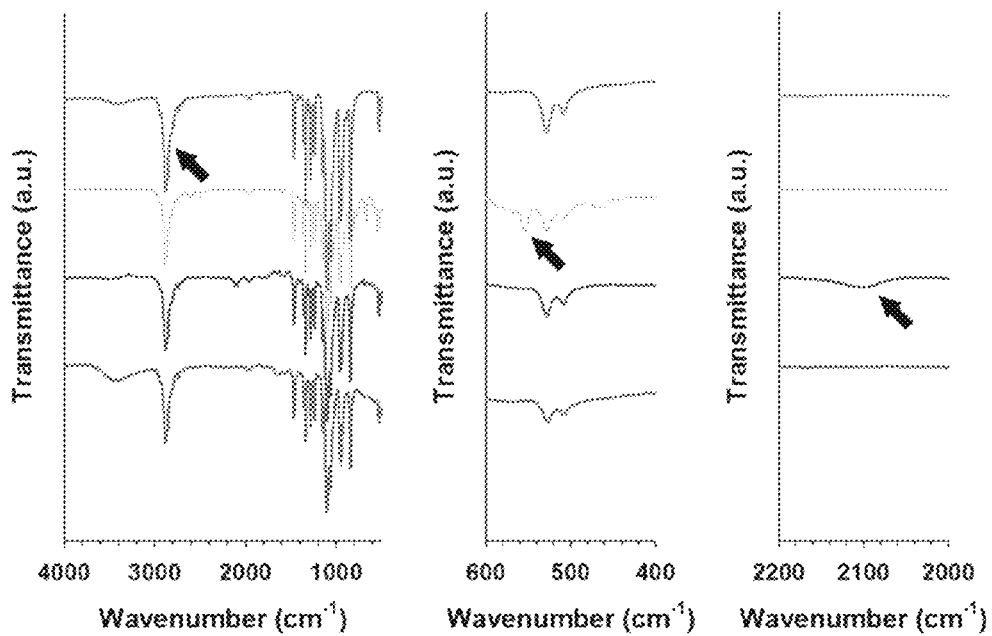
FIG. 3 illustrates an FT-IR confirmation result in a process of modifying mPEG-OH used in the synthesis of an amphiphilic block copolymer into mPEG-NH$_2$ (mPEG-OH→mPEG-TsCl→mPEG-N$_3$→mPEG-NH$_2$). Here, in the four lines in the view, the line indicated by the uppermost, the line indicated by the arrow right below the uppermost arrow, the line indicated by the next arrow, and the bottom line show the FT-IR confirmation results of mPEG, mPEG-TsCl, mPEG-N$_3$, and mPEG-NH$_2$, respectively. The peak at 2850 cm$^{-1}$ indicates CH$_3$ of mPEG (indicated by an arrow at the left side), the peak at 560 cm$^{-1}$ indicates S—O of mPEG-TsCl (indicated by an arrow in the middle), and the peak at 2103 cm$^{-1}$ indicates N$_3$ of mPEG-N$_3$ (indicated by an arrow at the right side).
Figure 4:
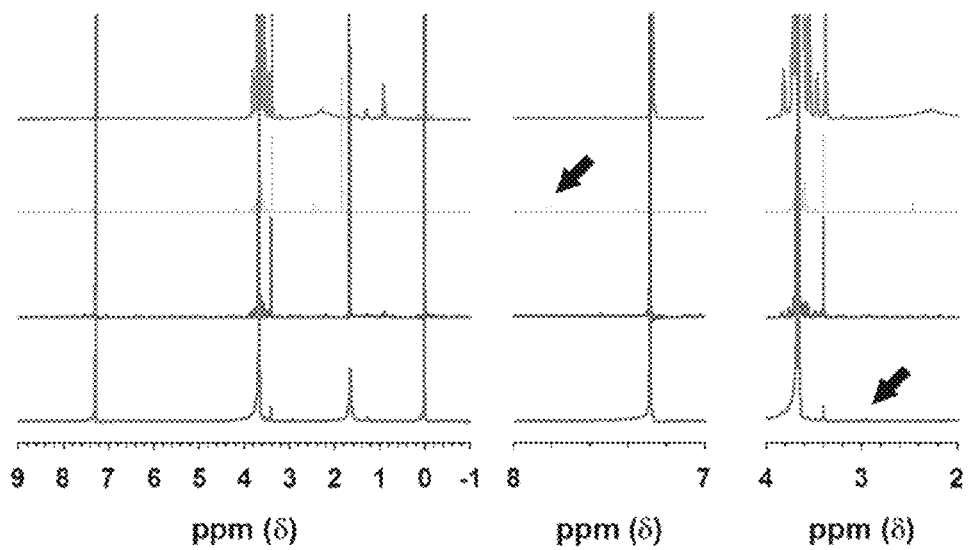
FIG. 4 illustrates an NMR confirmation result in a process of modifying mPEG-OH used in the synthesis of an amphiphilic block copolymer into mPEG-NH$_2$ (mPEG-OH→mPEG-TsCl→mPEG-N$_3$→mPEG-NH$_2$). Here, in the four lines in the view, the line indicated by the uppermost arrow, the line indicated by the arrow right below the uppermost arrow, the next and third line, and the line indicated by the bottom arrow show the $^1$H NMR results of mPEG, mPEG-TsCl, mPEG-N$_3$, and mPEG-NH$_2$, respectively. The peaks at 7.79 and 7.49 ppm indicate 2H of TsCl (indicated by an arrow in the middle), and the peak at 2.90 ppm indicates CH$_2$—NH$_2$ of mPEG-NH$_2$ (indicated by an arrow at the right side).

FIGS. 3 and 4 and Table 2 illustrate FT-IR and NMR confirmation results in a process of modifying mPEG-OH used in the synthesis of an amphiphilic block copolymer into mPEG-NH$_2$ (mPEG-OH→mPEG-TsCl→mPEG-N$_3$→mPEG-NH$_2$).

Through the FT-IR of FIG. 3, it was confirmed that as CH$_3$ of mPEG at 2,850 cm$^{-1}$, S—O of mPEG-TsCl at 560 cm$^{-1}$, and N$_3$ of mPEG-N$_3$ at 2,103 cm$^{-1}$ were confirmed, modification had been made.

Further, through $^1$H-NMR in FIG. 4, it was confirmed that as 2H of mPEG-TsCl at 7.79 and 7.49 ppm and CH$_2$ of mPEG-NH$_2$ at 2.90 ppm were confirmed, modification had been made.

Characteristics of the modified mPEG-NH$_2$ are the result values shown in Table 2.

TABLE 2

| Nomenclature | Yield (%) | Conversion Yield (%) | Molecular weight (g/mol) | |
|---|---|---|---|---|
| | | | GPC | $^1$H-NMR |
| mPEG$_{2000}$ | — | 100 | 2000 | — |
| mPEG-TsCl | 88 | 93 | 1953 | 2168 |
| mPEG-N$_3$ | 84 | 99 | 1988 | 2074 |
| mPEG-NH$_2$ | 94 | 98 | 1988 | 2048 |

Figure 5:
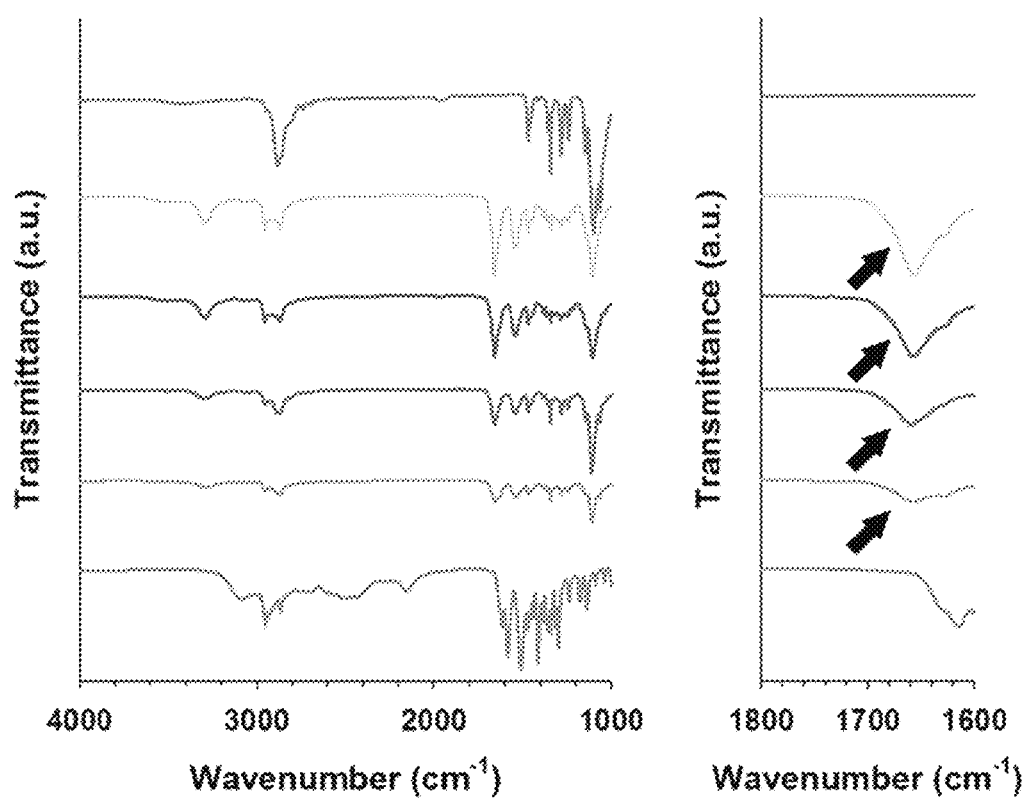
FIG. 5 illustrates the FT-IR confirmation result of mPEG-b-pLeu which is the amphiphilic block copolymer. Here, in the six lines in the view, the uppermost line, the next lower four lines, and the bottom line show the FT-IR results of mPEG, mPEG-b-pLeu, and DL-leucine, respectively. The peak at 1660 cm$^{-1}$ indicates an amide I bond of mPEG-b-pLeu (indicated by an arrow of the right view).
Figure 6:
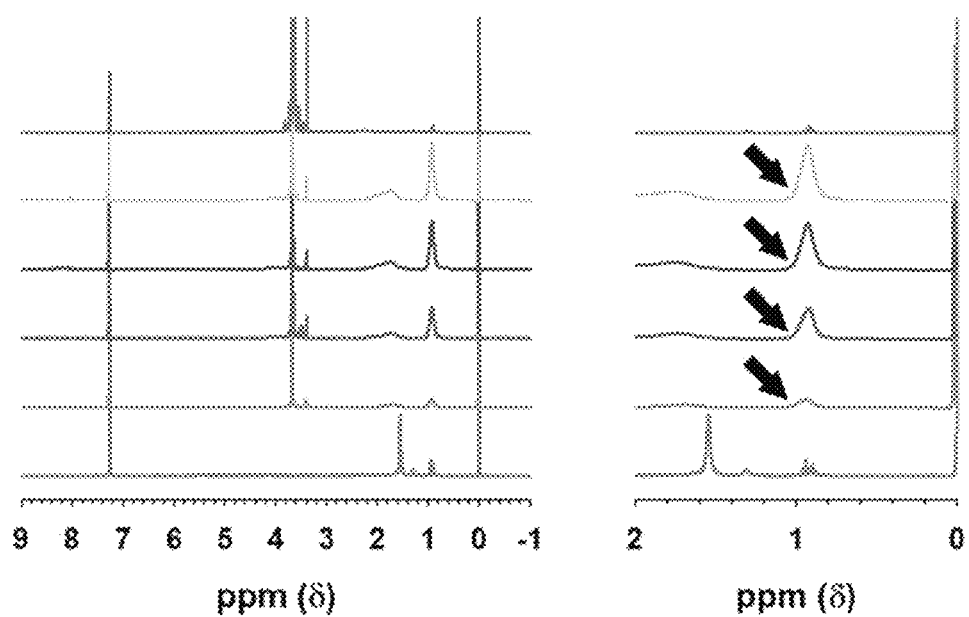
FIG. 6 illustrates the NMR confirmation result of the amphiphilic block copolymer, mPEG-b-pLeu. Here, in the six lines in the view, the uppermost line, the next lower four lines, and the bottom line shows the $^1$H NMR results of mPEG, mPEG-b-pLeu, and DL-leucine, respectively. The peak at 0.9 ppm indicates a methyl proton of polyleucine (indicated by an arrow of the right view).

FIGS. 5 and 6 illustrate the FT-IR and NMR confirmation results of the amphiphilic block copolymer mPEG-b-pLeu, and it could be seen through the FT-IR of FIG. 5 that an amide 1 bond and an amide 2 bond of mPEG-b-pLeu were confirmed at 1,660 and 1,754 cm$^{-1}$, and thus the synthesis had been made. Further, it could be seen through the NMR of FIG. 6 that CH$_3$ of mPEG-b-pLeu was confirmed at 0.9 ppm, and thus the synthesis had been made, and the molecular weight summarized in Table 2 could be confirmed.

Figure 7A:
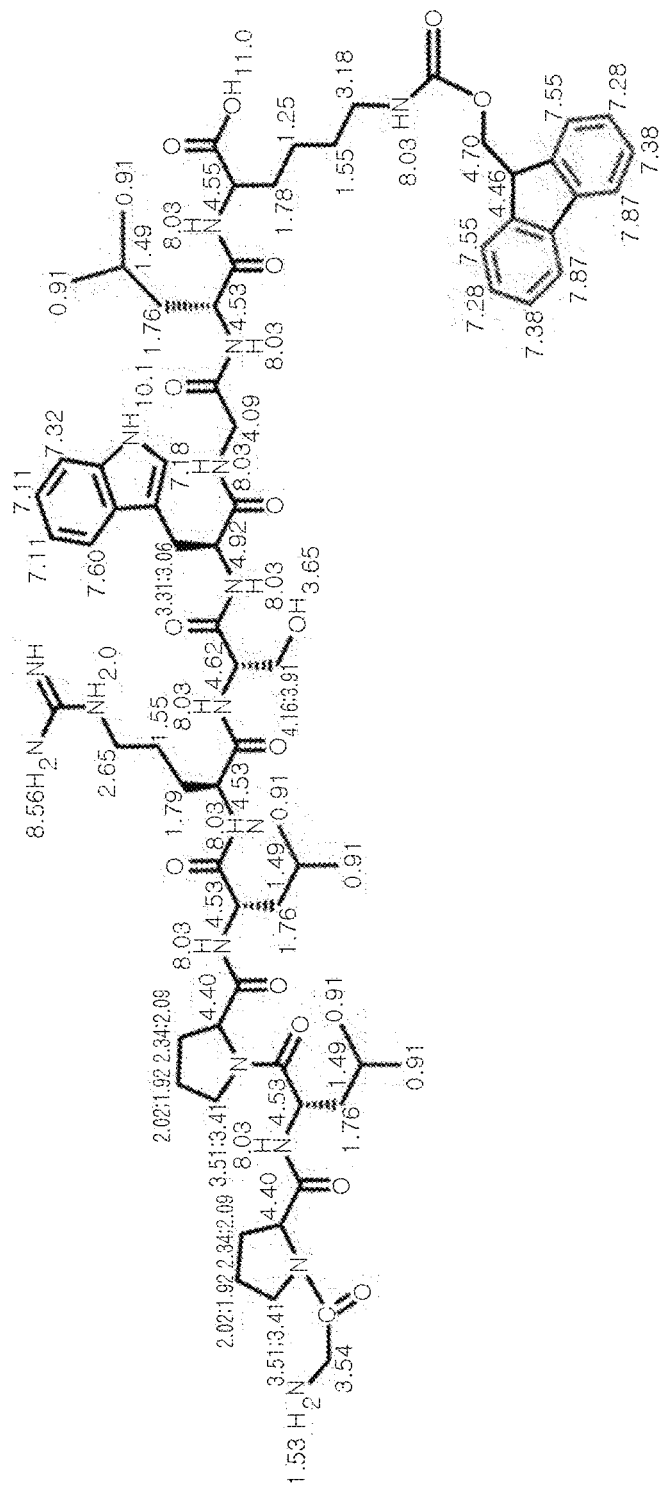
FIG. 7 illustrates the NMR confirmation result of the amphiphilic block copolymer MT1-MMP-b-pLeu. Here, a) indicates the chemical formula of MT1-MMP, the peak (arrow) at 7.55 ppm in the left upper graph of b) indicates 2CH$_2$ of MT1-MMP, and the peak (arrow) at 0.87 ppm in the right lower graph of b) indicates 2CH$_3$ of polyleucine.
Figure 7B:
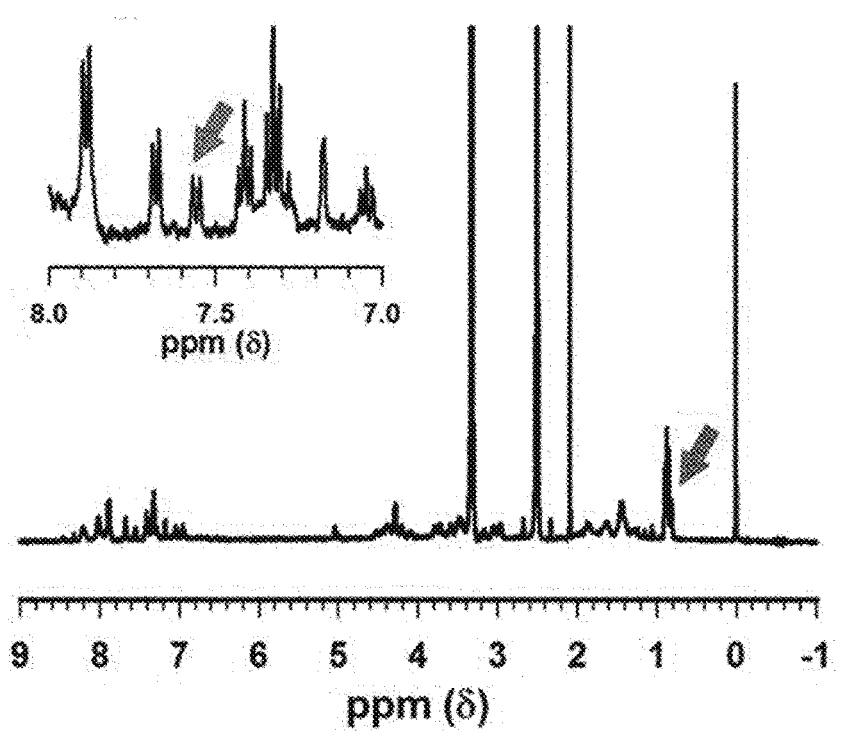
Figure 8A:
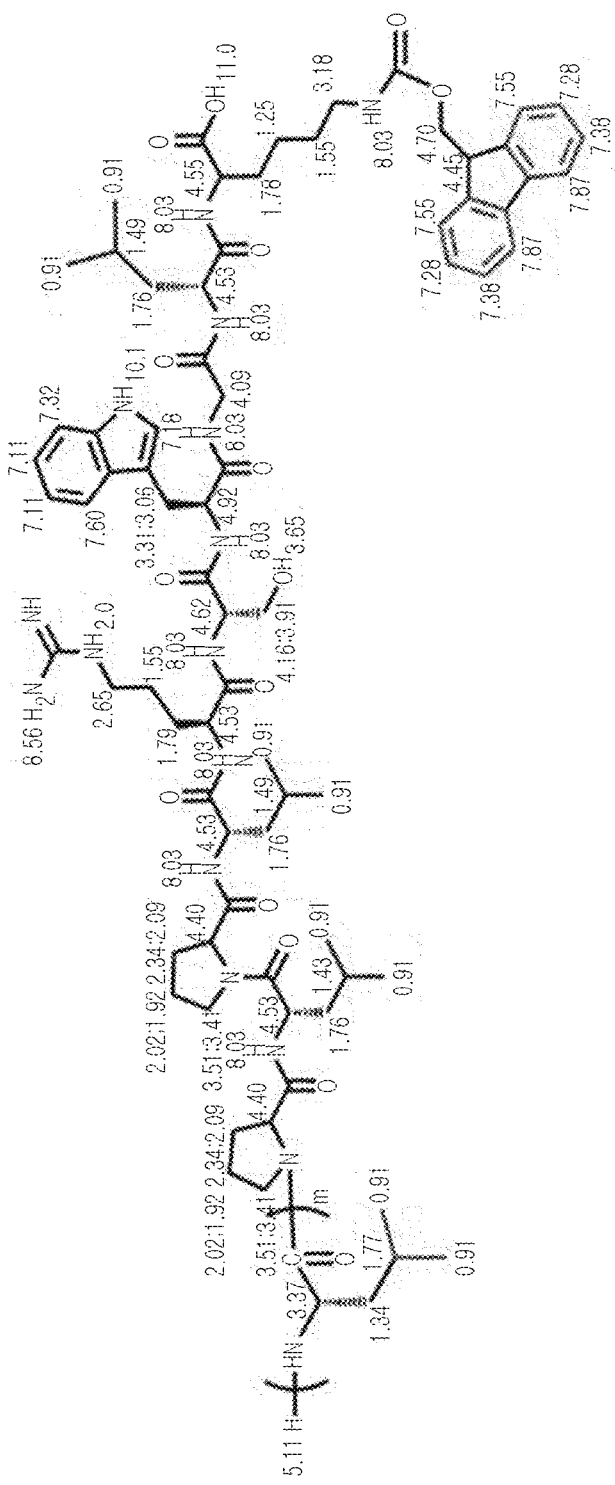
FIG. 8 illustrates a result of confirming NMR characteristics of the amphiphilic block copolymer, MT1-MMP-b-pLeu, and Leu-NCA, polyleucine, and MT1-MMP used in the synthesis of the block copolymer. Here, a) indicates the chemical formula of MT1-MMP, and in the five lines in the view of b), the uppermost line, the line right below the uppermost line, the next lower line, the third line and the bottom line indicate the NMR results of mPEG, Leu-NCA, polyleucine, MT1-b-pLeu, and MT1-MMP, respectively. The peak (arrow) at 7.55 ppm indicates 2CH$_2$ of MT1-MMP, the peak (arrow) at 4.3 ppm indicates 2CH$_3$ of polyleucine, and the peak (arrow) at 1.77 ppm indicates CH of DL-leucine.
Figure 8B:
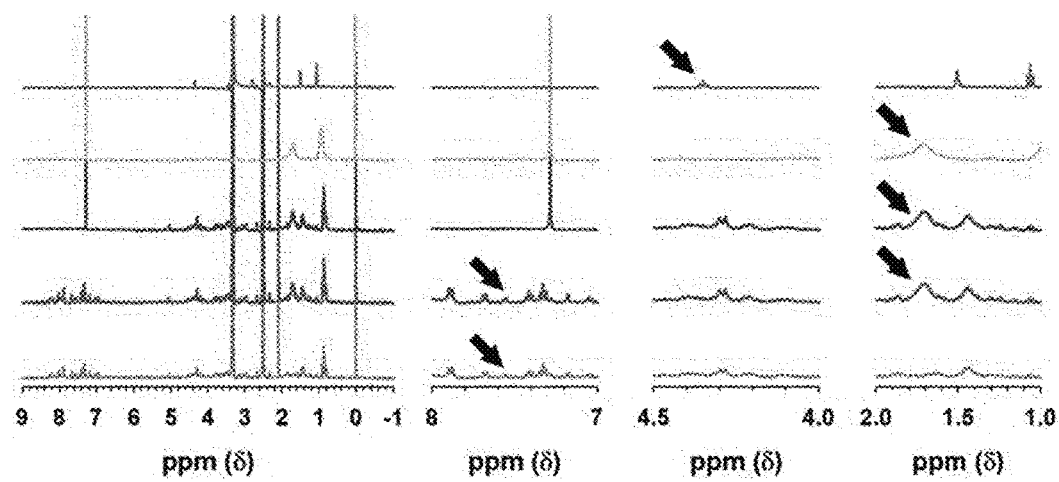
Figure 9A:
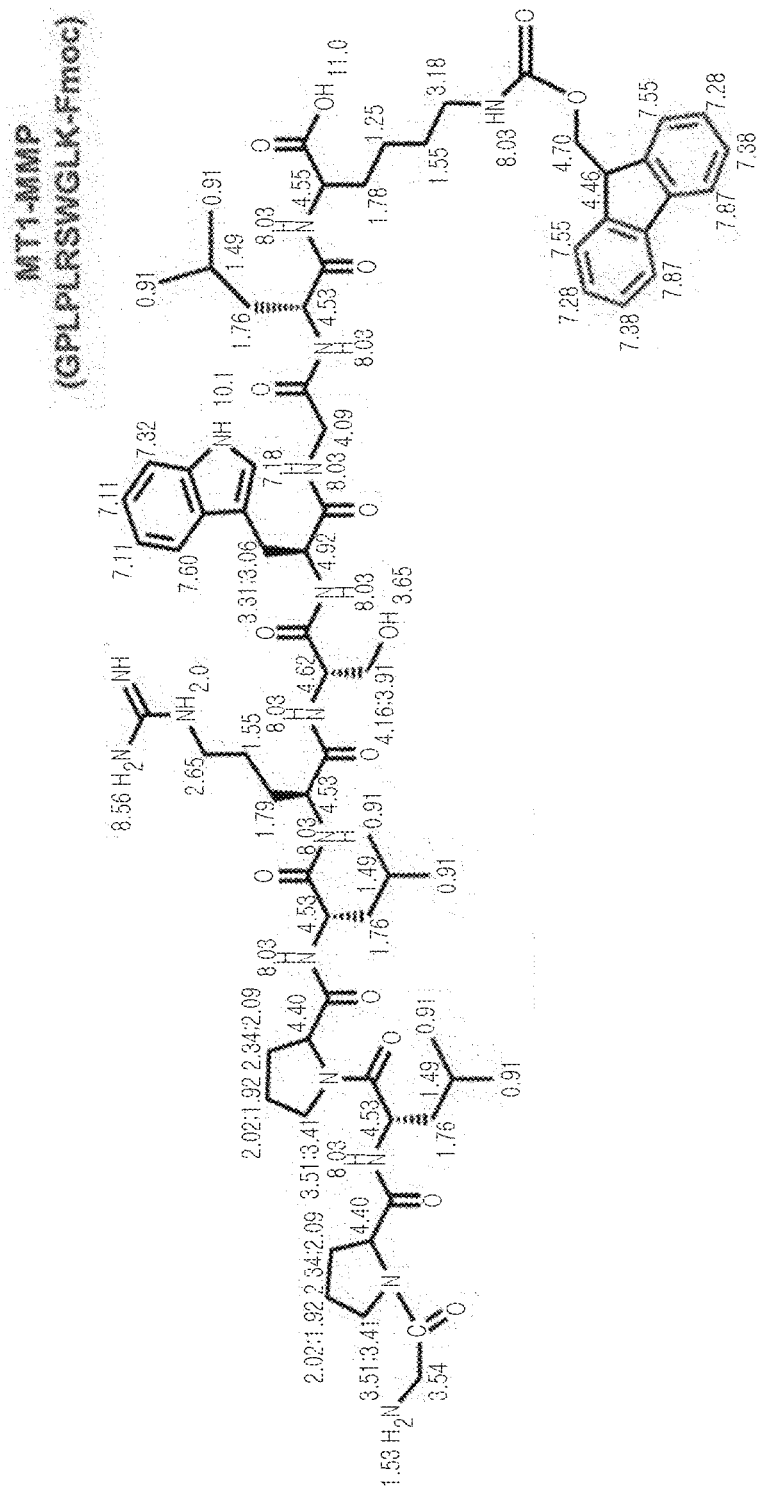
FIG. 9 illustrates an NMR result of confirming that Fmoc of MT1-MMP-b-pLeu used in the synthesis of the amphiphilic block copolymer, MT1-MMP-b-pLeu had been removed through the deprotection process. Here, a) indicates the chemical formula of MT1-MMP, and in the two graphs of b), the top graph and the bottom graph indicate the NMR results of MT1-b-pLeu and MT1-b-pLeu(Dep.), respectively.
Figure 9B:
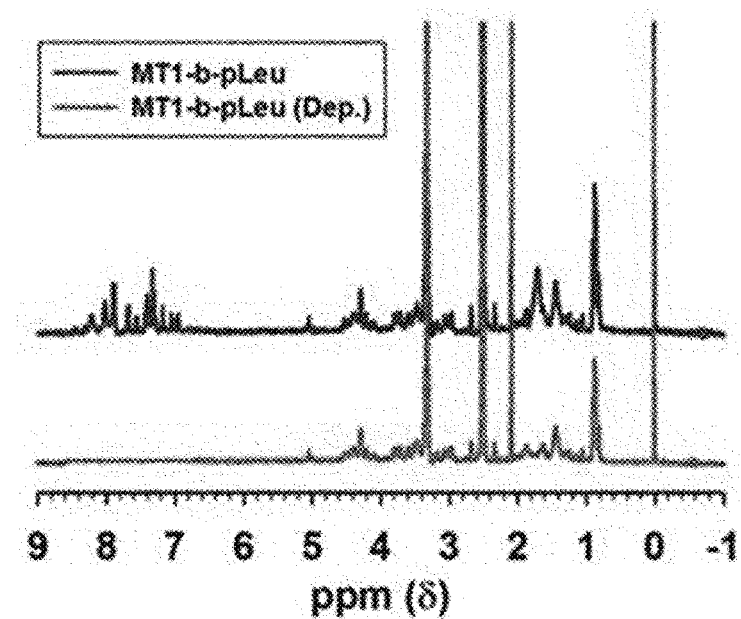

FIGS. 7 to 9 illustrate the results of confirming that the amphiphilic block copolymer MT1-MMP-b-pLeu was synthesized, and it was confirmed through the NMR of FIG. 7 that 2CH$_2$ and 2CH$_3$ of MT1-MMP were present at 7.55 and 0.87 ppm. FIG. 8 illustrates a result of confirming NMR characteristics of MT1-MMP-b-pLeu, and Leu-NCA, polyleucine, and MT1-MMP used in the synthesis of MT1-MMP-b-pLeu, and FIG. 9 illustrates a result of confirming that Fmoc of MT1-MMP-b-pLeu had been removed through the deprotection process as the peaks at 7 to 9 ppm disappeared.

Figure 10:
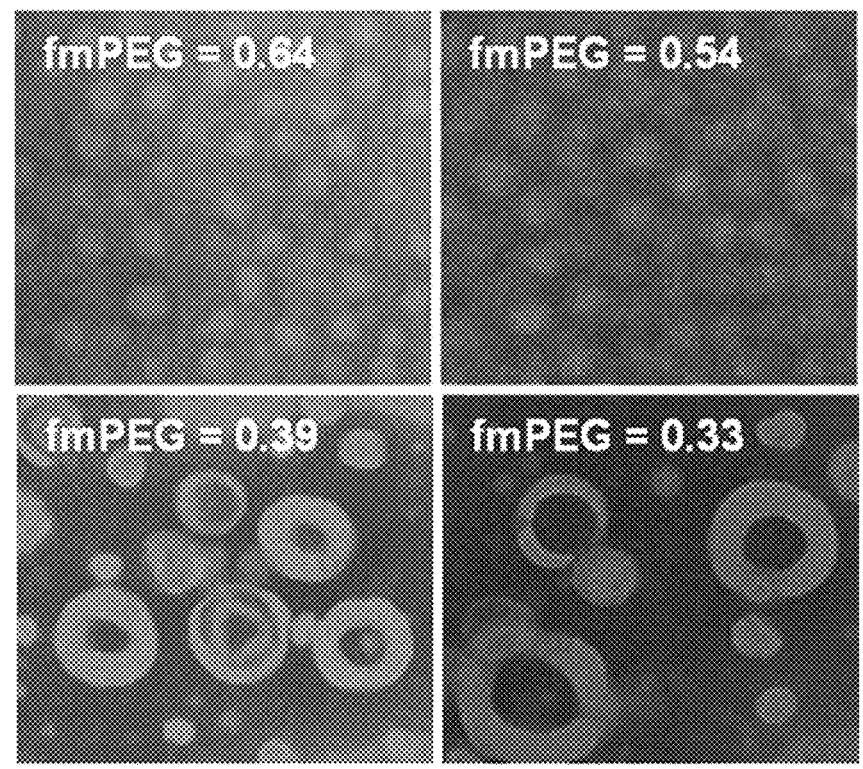
FIG. 10 illustrates TEM images of polymersomes formed of the amphiphilicblock copolymers, mPEG-b-pLeu and MT1-MMP-b-pLeu, according to the mPEG ratio (scale bar=100 nm).
Figure 11:
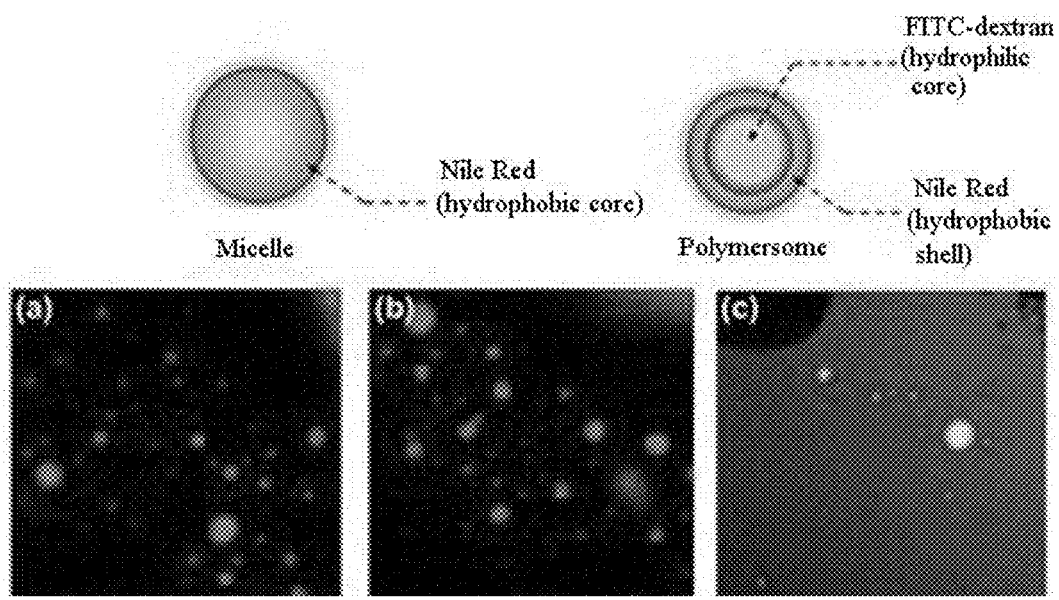
FIG. 11 illustrates confocal laser scanning microscopy (CLSM) images of a micelle or polymersome, which is formed of mPEG-b-pLeu and MT1-MMP-b-pLeu, which support a hydrophilic dye FITC-Dextran and a hydrophobic dye Nile Red (scale bar=5 μm), a) is a micelle supporting Nile Red, b) is a micelle supporting FITC-Dextran, and c) is a polymersome supporting FITC-Dextran and Nile Red.

Table 3 and FIGS. 10 and 11 are results showing that in the amphiphilic block copolymer mPEG-b-pLeu, the particle form varies depending on the ratio of a hydrophilic polymer and a polyamino acid which is a hydrophobic polymer, the synthesis was made by setting the mass fraction of the hydrophilic polymer (mPEG) to 0.33, 0.39, 0.54, and 0.64, and Table 3 summarizes the sizes of the amphiphilic nanoparticles of mPEG-b-pLeu and MT1-MMP-b-pLeu. In this case, in the amphiphilic block copolymer MT1-MMP-b-pLeu, the synthesis was also made by setting the mass fraction of the amphiphilic peptide to 0.34, 0.39, 0.55, and 0.65, and the mass fraction was calculated by the following Equation 1.

Mass fraction=Molecular weight of hydrophilic polymer or peptide/(Molecular weight of hydrophilic polymer or peptide+Molecular weight of hydrophobic polymer) [Equation 1]

Referring to FIG. 10, as a result of confirming the particle form according to each ratio through the TEM images, it could be seen that a micelle was formed at 0.64 and 0.54, and a polymersome was formed at 0.40. Further, even in FIG. 11, it was confirmed that a micelle was formed at 0.64 and 0.54 and a polymersome was formed at 0.40 in terms of particle form by supporting a hydrophilic dye FITC-Dextran and a hydrophobic dye Nile Red.

Figure 12:
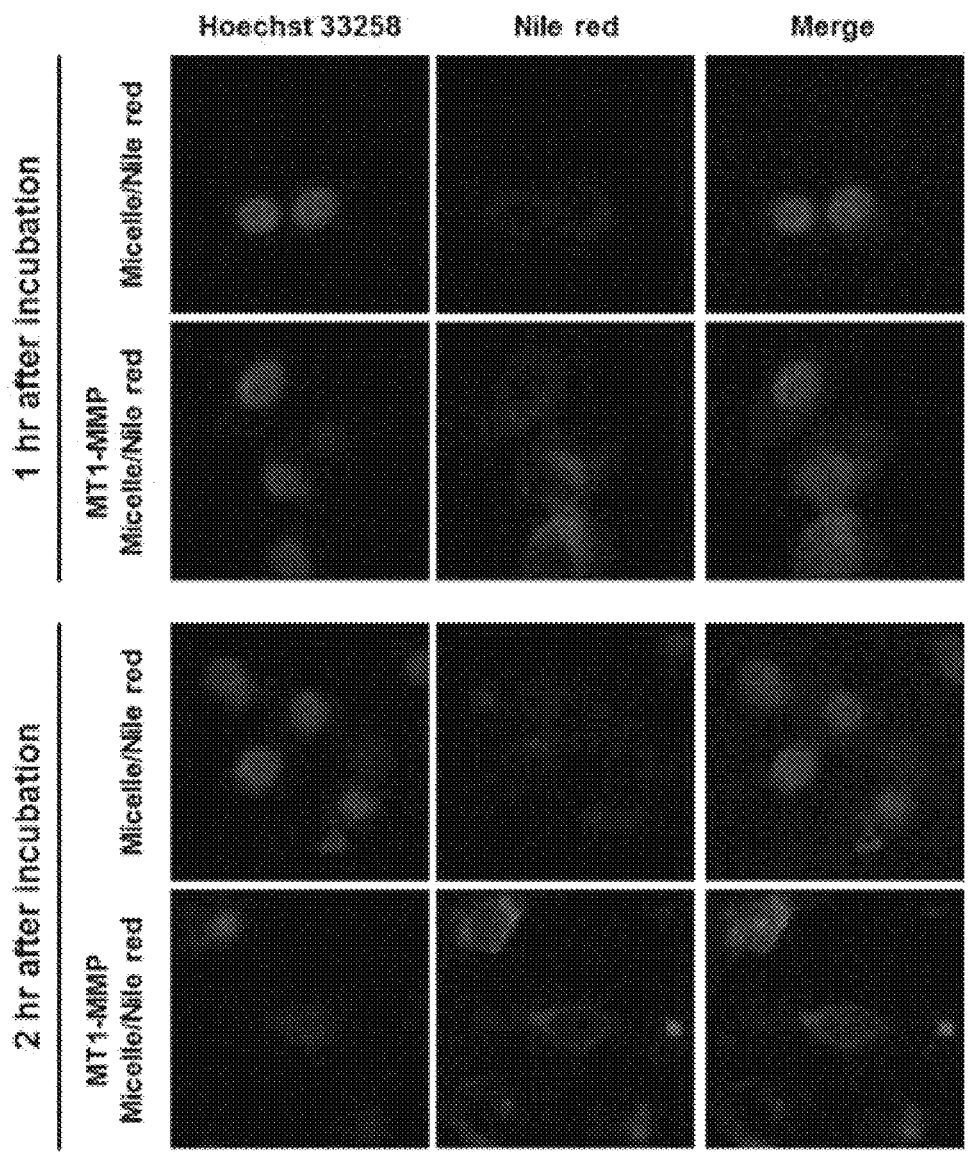
FIG. 12 illustrates a result of confirming the degrees of intracellular uptake of micelles formed of the amphiphilic block copolymers mPEG-b-pLeu and MT1-MMP-b-pLeu, and a micelle formed of only mPEG-b-pLeu through cell lines of HT-1080 in which MT1-MMP is highly expressed.

FIG. 12 illustrates a result of confirming the degrees of intracellular uptake of peptimicelles formed of the amphiphilic block copolymers MT1-MMP-b-pLeu and mPEG-b-pLeu, and a micelle formed of mPEG-b-pLeu through cell lines of HT-1080 in which MT1-MMP is highly expressed, and a pepti-micelle synthesized by setting the mass fraction of mPEG and MT1-MMP to 0.33 and 0.34, respectively was used. The blue color indicates a result that cells were stained with Hoechst 33258, and the red color indicates a pepti-micelle supporting Nile Red.

It can be seen that the intracellular uptake of a pepti-micelle composed of MT1-MMP-b-pLeu and mPEG-b-pLeu was good at a cultivation time of 1 hour and 2 hours.

Figure 13:
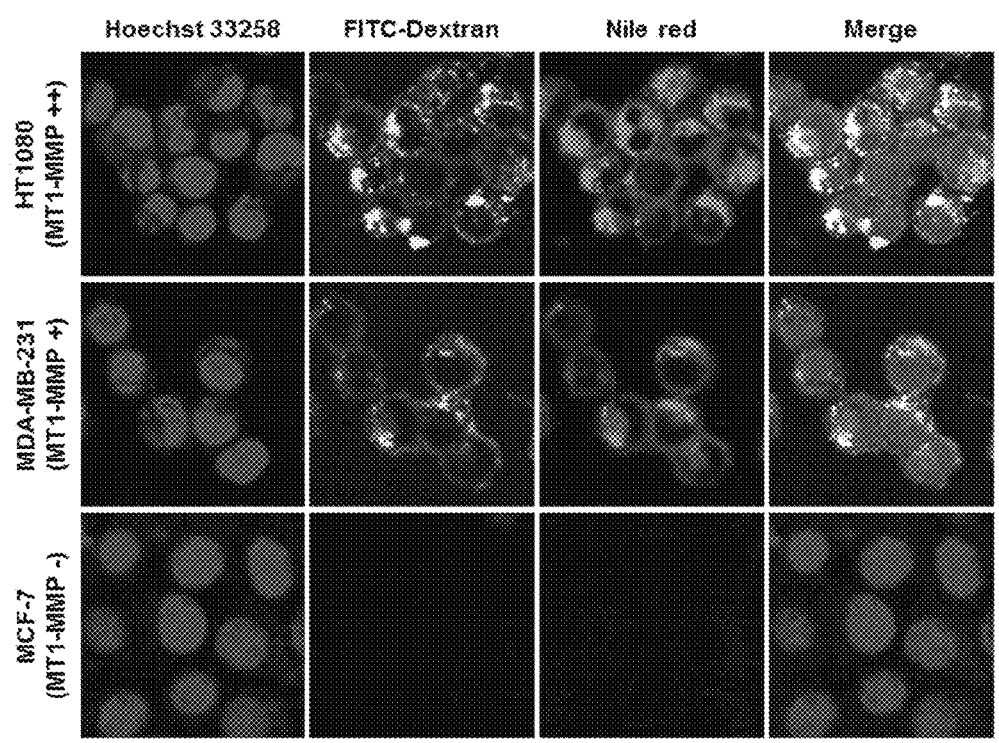
FIG. 13 illustrates a result of confirming the degree of intracellular uptake of polymersomes formed of the amphiphilic block copolymers mPEG-b-pLeu and MT1-MMP-b-pLeu through cell lines of HT-1080 (MT1-MMP++, overexpressed) in which MT1-MMP is highly expressed, MDA-MB-231 (MT1-MMP+, slightly expressed), and MCF-7 (MT1-MMP−, minimally expressed).

FIG. 13 illustrates a result of confirming the degree of intracellular uptake of polymersomes formed of the amphiphilic block copolymers mPEG-b-pLeu and MT1-MMP-b-pLeu in cell lines of HT-1080, MDA-MB-231, and MCF-7, and a pepti-polymersome synthesized by setting the mass fraction of mPEG and MT1-MMP to 0.40 and 0.39, respectively, was used. The blue color indicates a result that cells were stained with Hoechst 33258, the green color indicates a result that cells were stained with FITC-Dextran, and the red color indicates a pepti-polymersome supporting Nile Red. In FIG. 13, HT1080 (MT1-MMP++): MT1-MMP overexpressed (reference 100%), MDA-MB-231 (MT1-MMP+): MT1-MMP slightly expressed (19%), MCF-7 (MT1-MMP−): cell line in which MT1-MMP was minimally expressed (0.1%). The expression of MT1-MMP was confirmed through qRT-PCR by using the HT1080 cell line as the reference 100.

The pepti-polymersome composed of MT1-MMP-b-pLeu and mPEG-b-pLeu was effectively introduced into cells.

Figure 14:
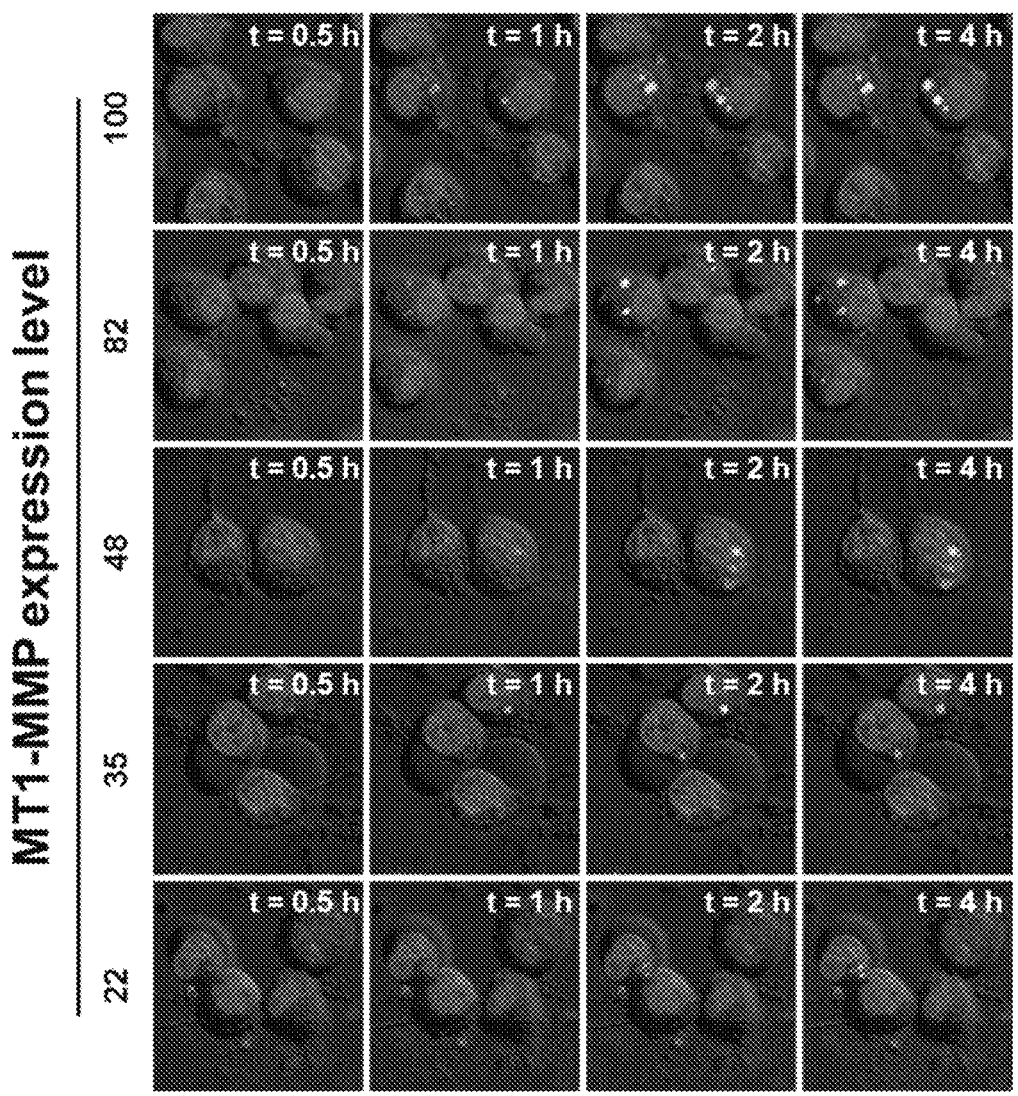
FIG. 14 illustrates a result of conducting intracellular uptake of a pepti-polymersome formed of mPEG-b-pLeu and MT1-MMP-b-pLeu, in which calcein is supported in the cell lines of HT-1080 in which the MT1-MMP expression rate is adjusted.

Further, as a result of introducing a pepti-polymersome formed of mPEG-b-pLeu and MT1-MMP-b-pLeu, which supported calcein in HT-1080 cell lines in which the MT1-MMP expression rate was adjusted by performing transfection using MT1-MMP siRNA into cells, it can be seen from the difference between fluorescence intensities that the higher the MT1-MMP expression rate was, the more the intracellular uptake of the pepti-polymersome was (FIG. 14).

TABLE 3

| mPEG mass fraction | Size (nm) |
| --- | --- |
| 0.33 | 179.3 ± 4.5 |
| 0.39 | 133.7 ± 4.8 |

TABLE 3-continued

| mPEG mass fraction | Size (nm) |
| --- | --- |
| 0.54 | 66.0 ± 2.8 |
| 0.64 | 55.9 ± 3.0 |

INDUSTRIAL APPLICABILITY

The present invention may be used in the diagnostic or therapeutic fields of a disease.

The invention claimed is:

1. An amphiphilic nanoparticle comprising:
   a block copolymer containing a hydrophilic polymer and a hydrophobic polymer (A); and
   a block copolymer containing a peptide cleaved by a proteolytic enzyme and a hydrophobic polymer (B).

2. The amphiphilic nanoparticle of claim 1, wherein the hydrophilic polymer is one or more selected from the group consisting of polyalkylene glycol, polyethylene oxide, polyoxazoline, poly(N-vinylpyrrolidone), polyvinyl alcohol, polyhydroxyethylmethacrylate, dextran, polyserine, polythreonine, polytyrosine, polylysine, polyarginine, polyhistidine, polyaspartic acid, and polyglutamic acid.

3. The amphiphilic nanoparticle of claim 1, wherein the hydrophilic polymer comprises methoxy amino polyethylene glycol.

4. The amphiphilic nanoparticle of claim 1, wherein the hydrophobic polymer is a homopoly amino acid represented by the following Chemical Formula 1:

$$(poly-M)n$$

here,
M is leucine, isoleucine, valine, phenylalanine, proline, glycine, or methionine, and n represents 10 to 100.

5. The amphiphilic nanoparticle of claim 1, wherein the peptide cleaved by a proteolytic enzyme comprises any one the amino acid sequence selected from the group consisting of GPLPLRSW/GLK (SEQ ID NO.: 1), PLG/LR (SEQ ID NO.: 2), VPLS/LTM (SEQ ID NO.: 3), PLG/MRG (SEQ ID NO.: 4), K/K (SEQ ID NO.: 5), PICF/FRL (SEQ ID NO.: 6), HSSLQ (SEQ ID NO.: 7), WEHD (SEQ ID NO.: 8), DEVD (SEQ ID NO.: 9), F(Pip)R/S (SEQ ID NO.: 10), NQ/EQVS (SEQ ID NO.: 11), GP/GP (SEQ ID NO.: 12), and GVSQNY/PIVG (SEQ ID NO.: 13).

6. The amphiphilic nanoparticle of claim 1, wherein the amphiphilic nanoparticle has an average particle diameter of 50 to 200 nm in diameter.

7. The amphiphilic nanoparticle of claim 1, wherein the amphiphilic nanoparticle is in a form of polymersomes or micelles.

8. The amphiphilic nanoparticle of claim 1, further comprising a fluorescent material.

9. The amphiphilic nanoparticle of claim 1, further comprising a pharmaceutically active component.

10. A method for preparing the amphiphilic nanoparticle of claim 1, the method comprising:
    reacting a block copolymer containing a hydrophilic polymer and a hydrophobic polymer (A) with a block copolymer containing a peptide cleaved by a proteolytic enzyme and a hydrophobic polymer (B).

11. The method of claim 10, wherein the amphiphilic nanoparticle is a polymersome synthesized by comprising a hydrophilic polymer or peptide having a mass fraction of 25 to 40, which is calculated according to the following Equation 1:

Mass fraction=Molecular weight of hydrophilic polymer or peptide/(Molecular weight of hydrophilic polymer or peptide+Molecular weight of hydrophobic polymer).

12. The method of claim 10, wherein the amphiphilic nanoparticle is a micelle structure synthesized by comprising a hydrophilic polymer or peptide having a mass fraction of more than 40 and 70 or less, which is calculated according to the following Equation 1:

Mass fraction=Molecular weight of hydrophilic polymer or peptide/(Molecular weight of hydrophilic polymer or peptide+Molecular weight of hydrophobic polymer).

13. A composition for activity or quantitative analysis of a proteolytic enzyme, comprising:
    the amphiphilic nanoparticle of claim 1.

14. The composition of claim 13, wherein the proteolytic enzyme is one of matrix metalloproteinases (MMPs), thrombin, factor Xiiia (FXIIIa), caspase, urokinase plasminogen activator (uPA), Fijian, cathepsins, HIV protease, dipeptidyl peptidase (DPP-IV), or proteasome.

15. A target directed-type contrast agent composition comprising:
   the amphiphilic nanoparticle of claim 1; and
   a pharmaceutically acceptable carrier.

16. A contrast agent composition for simultaneous diagnosis or treatment, comprising:
   the amphiphilic nanoparticle of claim 1; and
   a pharmaceutically acceptable carrier.

17. A multi-diagnosis probe comprising:
   the amphiphilic nanoparticle of claim 1; and
   a diagnosis probe for image interpretation.

* * * * *